US00PP30398P2

(12) United States Plant Patent
Rebello

(10) Patent No.: US PP30,398 P2
(45) Date of Patent: Apr. 16, 2019

(54) ***XEROCHRYSUM* PLANT NAMED 'BONXERO 148'**

(50) Latin Name: *Xerochrysum bracteatum*
Varietal Denomination: Bonxero 148

(71) Applicant: Shaun L. Rebello, Blair Athol (AU)

(72) Inventor: Shaun L. Rebello, Blair Athol (AU)

(73) Assignee: Bonza Botanicals Pty., Ltd., Yellow Rock, NSW (AU)

( * ) Notice: Subject to any disclaimer, the term of this patent is extended or adjusted under 35 U.S.C. 154(b) by 0 days.

(21) Appl. No.: 15/732,830

(22) Filed: Jan. 3, 2018

(51) Int. Cl.
*A01H 5/02* (2018.01)

(52) U.S. Cl.
USPC ..... Plt./359

(58) Field of Classification Search
USPC ..... Plt./359
See application file for complete search history.

*Primary Examiner* — Susan McCormick Ewoldt
(74) *Attorney, Agent, or Firm* — C. A. Whealy

(57) ABSTRACT

A new and distinct cultivar of *Xerochrysum* plant named 'Bonxero 148', characterized by its upright, mounding and uniform plant habit; vigorous growth habit; freely flowering habit; large inflorescences with bright yellow-colored involucral bracts; and strong peduncles that hold the inflorescences above the foliar plane.

1 Drawing Sheet

Botanical designation: *Xerochrysum bracteatum.*
Cultivar denomination: 'BONXERO 148'.

BACKGROUND OF THE INVENTION

The present invention relates to a new and distinct cultivar of *Xerochrysum* plant, botanically known as *Xerochrysum bracteatum*, and hereinafter referred to by the name 'Bonxero 148'.

The new *Xerochrysum* plant is a product of a planned breeding program conducted by the Inventor in Yellow Rock, New South Wales, Australia. The objective of the breeding program is to create and develop new upright *Xerochrysum* cultivars with uniformly mounded plant habit, freely flowering habit and large attractive inflorescences.

The new *Xerochrysum* plant originated from a cross-pollination by the Inventor on Apr. 30, 2013 of a proprietary selection of *Xerochrysum bracteatum* identified as code number 00-186, not patented, as the female, or seed, parent with a proprietary selection of *Xerochrysum bracteatum* identified as code number 00-37.90, not patented, as the male, or pollen, parent. The new *Xerochrysum* was discovered and selected by the Inventor as a single flowering plant within the progeny of the stated cross-pollination in a controlled greenhouse environment in Yellow Rock, New South Wales, Australia on Apr. 11, 2014.

Asexual reproduction of the new *Xerochrysum* plant by terminal cuttings in a controlled greenhouse environment in Yellow Rock, New South Wales, Australia since April, 2014, has shown that the unique features of this new *Xerochrysum* plant are stable and reproduced true to type in successive generations.

SUMMARY OF THE INVENTION

Plants of the new *Xerochrysum* have not been observed under all possible combinations of environmental and cultural conditions. The phenotype may vary somewhat with variations in environment such as temperature and light intensity, without, however, any variance in genotype.

The following traits have been repeatedly observed and are determined to be the unique characteristics of 'Bonxero 148'. These characteristics in combination distinguish 'Bonxero 148' as a new and distinct *Xerochrysum* plant:

1. Upright, mounding and uniform plant habit.
2. Vigorous growth habit.
3. Freely flowering habit.
4. Large inflorescences with bright yellow-colored involucral bracts.
5. Strong peduncles that hold the inflorescences above the foliar plane.

In side-by-side comparisons, plants of the new *Xerochrysum* differ primarily from plants of the female parent selection in the following characteristics:

1. Plants of the new *Xerochrysum* are more vigorous than plants of the female parent selection.
2. Plants of the new *Xerochrysum* have larger inflorescences than plants of the female parent selection.

In side-by-side comparisons, plants of the new *Xerochrysum* differ primarily from plants of the male parent selection in the following characteristics:

1. Plants of the new *Xerochrysum* are more vigorous than plants of the male parent selection.
2. Plants of the new *Xerochrysum* have larger inflorescences than plants of the male parent selection.

Plants of the new *Xerochrysum* can be compared to plants of the *Bracteantha bracteata* 'OHB003790', disclosed in U.S. Plant Pat. No. 15,629. In side-by-side comparisons, plants of the new *Xerochrysum* differ primarily from plants of 'OHB003790' in the following characteristics:

1. Plants of the new *Xerochrysum* are larger and more vigorous than plants of 'OHB003790'.
2. Plants of the new *Xerochrysum* have larger leaves than plants of 'OHB003790'.
3. Plants of the new *Xerochrysum* have larger inflorescences than plants of 'OHB003790'.
4. Inflorescences of plants of the new *Xerochrysum* have more involucral bracts and disc florets than inflorescences of plants of 'OHB003790'.

BRIEF DESCRIPTION OF THE PHOTOGRAPHS

The accompanying photographs illustrate the overall appearance of the new *Xerochrysum* plant. These photographs show the colors as true as it is reasonably possible to obtain in colored reproductions of this type. Colors in the photographs may differ slightly from the color values cited in the detailed botanical description which accurately describe the colors of the new *Xerochrysum* plant.

The photograph at the top of the sheet comprises a side perspective view of a typical flowering plant of 'Bonxero 148' grown in a container.

The photograph at the bottom of the sheet comprises a close-up view of a typical inflorescence of 'Bonxero 148'.

DETAILED BOTANICAL DESCRIPTION

The aforementioned photographs and following observations and measurements describe plants grown during the summer in 20-cm container in an outdoor nursery in Higashiomi, Shiga, Japan and under conditions and practices which approximate those generally used in commercial *Xerochrysum* production. During the production of the plants, day temperatures averaged 23° C. and night averaged 13° C. Measurements and numerical values represent averages for typical flowering plants. Plants were about four months old when the photographs were taken and five months old when the detailed description was taken. In the following description, color references are made to The Royal Horticultural Society Colour Chart, 2001 Edition, except where general terms of ordinary dictionary significance are used.

Botanical classification: *Xerochrysum bracteatum* 'Bonxero 148'.

Parentage:

*Female, or seed, parent*.—Proprietary selection of *Xerochrysum bracteatum* identified as code number 00-186, not patented.

*Male, or pollen, parent*.—Proprietary selection of *Xerochrysum bracteatum* identified as code number 00-37.90, not patented.

Propagation:

*Type*.—Terminal vegetative cuttings.

*Time to initiate roots, summer*.—About seven days at temperatures about 18° C. to 21° C.

*Time to initiate roots, winter*.—About ten days at temperatures about 18° C. to 21° C.

*Time to produce a rooted cutting, summer*.—About three weeks at temperatures about 18° C. to 21° C.

*Time to produce a rooted cutting, winter*.—About four weeks at temperatures about 18° C. to 21° C.

*Root description*.—Fibrous; typically white in color, actual color of the roots is dependent on substrate composition, water quality, fertilizer type and formulation, substrate temperature and physiological age of roots.

*Rooting habit*.—Freely branching; moderately dense.

Plant description:

*Plant form and growth habit*.—Upright, mounding and uniform plant habit with inflorescences held above the foliage on strong peduncles; vigorous growth habit.

*Plant height*.—About 43 cm.

*Plant diameter or spread*.—About 53 cm.

*Lateral branches*.—Quantity per plant: Freely branching habit with about seven lateral branches per plant. Length: About 14 cm. Diameter: About 6.2 mm. Internode length: About 2.3 cm. Aspect: Upright to slightly outwardly. Strength: Strong. Texture: Rough, pubescent. Color: Close to 143B.

*Leaf description*.—Arrangement: Alternate, simple; sessile. Length: About 8.7 cm. Width: About 2.5 cm. Shape: Lanceolate. Apex: Acute. Base: Attenuate. Margin: Entire. Texture, upper and lower surfaces: Rough, pubescent. Venation pattern: Pinnate; reticulate. Color: Developing leaves, upper surface: Close to NN137B. Developing leaves, lower surface: Close to 137B. Fully expanded leaves, upper surface: Close to NN137B; venation, close to 147D. Fully expanded leaves, lower surface: Close to 147B; venation, close to 147C.

Inflorescence description:

*Appearance*.—Terminal double-type inflorescence form with lanceolate involucral bracts; involucral bracts and disc florets developing acropetally on a capitulum; inflorescences positioned above the foliar plane on strong peduncles; inflorescences face mostly upright.

*Flowering habit*.—Freely flowering habit; about 35 to 40 inflorescences develop per plant during the flowering season.

*Fragrance*.—None detected.

*Time to flower*.—In Japan, plants begin to flower about 21 weeks after planting and in the garden, plant flower continuously from the spring through autumn.

*Post-production longevity*.—Inflorescences maintain good substance for about 18 days on the plant; inflorescences persistent.

*Inflorescence buds*.—Height: About 1.9 cm. Diameter: About 1.3 cm. Shape: Ovoid. Color: Close to 9B and 163A.

*Inflorescence size*.—Diameter: About 7 cm. Depth (height): About 3 cm. Disc diameter: About 2.2 cm. Disc height: About 4.3 mm.

*Involucral bracts*.—Quantity per inflorescence and arrangement: About 300 arranged in numerous whorls. Length: About 1.8 cm. Width: About 7.3 mm. Shape: Narrowly ovate. Apex: Acute. Base: Truncate. Margin: Entire. Texture and luster, upper and lower surfaces: Smooth, glabrous; papery; glossy. Orientation: Initially upright becoming horizontal with development. Color: When opening and fully opened, upper surface: Close to 3A. When opening and fully opened, lower surface: Close to 3A.

*Disc florets*.—Quantity per inflorescence and arrangement: About 1,300 spirally arranged in the center of the receptacle. Length: About 1.2 cm. Diameter, distally: About 2.2 mm. Diameter, proximally: About 1 mm. Shape: Tubular; apex dentate, five-pointed. Texture, inner and outer surfaces: Smooth, glabrous. Color: When developing, inner surface: Close to 151D. When developing, outer surface: Close to 23A. Fully developed, inner and outer surfaces: Close to 23A; towards the base, close to 4D.

*Peduncles*.—Length: About 18 cm. Diameter: About 3.3 mm. Strength: Strong. Aspect: Upright to slightly outwardly. Texture: Rough, pubescent. Color: Close to 146A.

*Reproductive organs* (*present on disc florets only*).—Androecium: Quantity per disc floret: About five. Filament length: About 6 mm. Filament color: Close to 157D. Anther size: About 3.5 mm by 0.6 mm. Anther shape: Lanceolate. Anther color: Close to 14A. Pollen amount: Moderate. Pollen color: Close to 13B. Gynoecium: Pistil length: About 1 cm. Stigma shape: Bi-parted. Stigma color: Close to 14B. Style color: Distally, close to 14B; proximally, close to 157D. Ovary color: Close to 155A.

*Seeds and fruits*.—Seed and fruit production has not been observed on plants of the new *Xerochrysum* to date.

Pathogen & pest resistance: Plants of the new *Xerochrysum* have not been shown to be resistant to pathogens and pests common to *Xerochrysum* to date.

Temperature tolerance: Plants of the new *Xerochrysum* have been observed to tolerate temperatures ranging from about 0° C. to about 35° C.

It is claimed:

1. A new and distinct *Xerochrysum* plant named 'Bonxero 148' as illustrated and described.

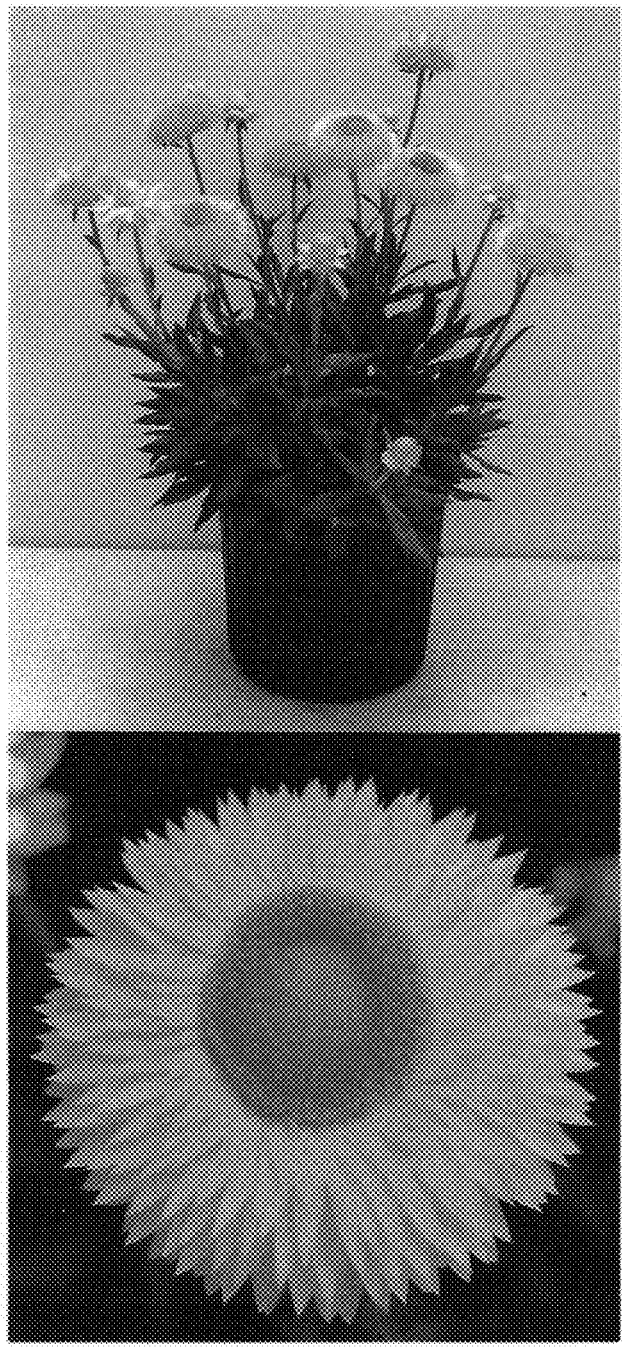

* * * * *